(12) United States Patent
Karimpour

(10) Patent No.: US 11,019,804 B2
(45) Date of Patent: Jun. 1, 2021

(54) AUTOMATIC SYSTEM AND METHOD FOR DELIVERING A SUBSTANCE TO AN ANIMAL

(71) Applicant: Applied LifeSciences and Systems, LLC, Raleigh, NC (US)

(72) Inventor: Ramin Karimpour, Raleigh, NC (US)

(73) Assignee: Applied LifeSciences & Systems, LLC, Raleigh, NC (US)

( * ) Notice: Subject to any disclaimer, the term of this patent is extended or adjusted under 35 U.S.C. 154(b) by 275 days.

(21) Appl. No.: 15/775,608

(22) PCT Filed: Nov. 11, 2016

(86) PCT No.: PCT/US2016/061548
§ 371 (c)(1),
(2) Date: May 11, 2018

(87) PCT Pub. No.: WO2017/083663
PCT Pub. Date: May 18, 2017

(65) Prior Publication Data
US 2018/0343830 A1 Dec. 6, 2018

Related U.S. Application Data

(60) Provisional application No. 62/349,981, filed on Jun. 14, 2016, provisional application No. 62/254,737, filed on Nov. 13, 2015.

(51) Int. Cl.
*A01K 13/00* (2006.01)
*A01K 45/00* (2006.01)
(Continued)

(52) U.S. Cl.
CPC .......... *A01K 13/003* (2013.01); *A01K 45/00* (2013.01); *A01K 61/13* (2017.01); *A61B 5/0077* (2013.01);
(Continued)

(58) Field of Classification Search
CPC ...... A01K 13/003; A01K 45/007; A61D 7/00; A61D 1/025; A01D 7/00; A61B 5/70
See application file for complete search history.

(56) References Cited

U.S. PATENT DOCUMENTS 1,505,641 A * 8/1924 Hendrickson ........ A01K 13/003
119/667
3,661,259 A 5/1972 Reynolds
(Continued)

FOREIGN PATENT DOCUMENTS

CN 105361973 A 3/2016
FR 2885030 B1 11/2006
(Continued)

OTHER PUBLICATIONS

Office Action issued by Federal Service for Intellectual Property (Russia) against Application No. 2018117356/10(027024) dated Mar. 4, 2020.
(Continued)

*Primary Examiner* — Christopher D Hutchens
(74) *Attorney, Agent, or Firm* — Kathleen M. Lynch

(57) ABSTRACT

A system and method for automatically delivering a substance to an animal including a positioning system that positions each animal singularly, a sensor that detects the location of a predetermined targeted area on the animal and an image processor. The system further includes a delivery device having a plurality of delivery outlets for delivering a substance to the targeted area. The sensor, image processor and delivery device are in communication with a computer processor. The sensor activates the image processor which takes at least one image of the animal positioned singularly. The image is communicated to the computer processor and analyzed. The computer processor activates the delivery outlet proximate the predetermined target area on the animal
(Continued)

which delivers an effective dosage of substance to the predetermined targeted area.

13 Claims, 10 Drawing Sheets

(51) Int. Cl.
*A61B 5/00* (2006.01)
*A61D 7/00* (2006.01)
*G16H 50/20* (2018.01)
*A61D 17/00* (2006.01)
*A61D 19/00* (2006.01)
*A61D 1/02* (2006.01)
*B65G 15/30* (2006.01)
*A61D 3/00* (2006.01)
*G06T 7/00* (2017.01)
*A01K 61/13* (2017.01)
*G16H 20/17* (2018.01)
*A61M 5/30* (2006.01)
*A61M 5/42* (2006.01)

(52) U.S. Cl.
CPC .................. *A61B 5/43* (2013.01); *A61B 5/70* (2013.01); *A61B 5/7282* (2013.01); *A61D 1/025* (2013.01); *A61D 3/00* (2013.01); *A61D 7/00* (2013.01); *A61D 17/00* (2013.01); *A61D 19/00* (2013.01); *A61M 5/30* (2013.01); *A61M 5/427* (2013.01); *B65G 15/30* (2013.01); *G06T 7/001* (2013.01); *G16H 20/17* (2018.01); *G16H 50/20* (2018.01); *A61B 2503/40* (2013.01); *A61B 2576/00* (2013.01); *A61M 2250/00* (2013.01); *B65G 2201/02* (2013.01); *G06T 2207/30128* (2013.01); *Y02A 90/10* (2018.01)

(56) References Cited

U.S. PATENT DOCUMENTS

| | | |
|---|---|---|
| 3,777,752 A | 12/1973 | Goodwin |
| 3,994,292 A | 11/1976 | Goodwin |
| 4,316,464 A | 2/1982 | Peterson |
| 4,449,968 A | 5/1984 | Peterson |
| 4,674,490 A | 6/1987 | Frankel et al. |
| 4,850,997 A | 7/1989 | DuBose |
| 4,947,802 A | 8/1990 | Fisinin |
| 5,312,353 A | 5/1994 | Boggess et al. |
| 5,626,101 A | 5/1997 | Kuhl |
| 6,396,938 B1 | 5/2002 | Tao et al. |
| 6,634,319 B1 | 10/2003 | Zermoglio et al. |
| 6,910,446 B2 | 6/2005 | Johnston, Jr. |
| 6,974,373 B2 | 12/2005 | Kriessel |
| 7,004,112 B2 | 2/2006 | Gorans |
| 7,802,541 B2 | 9/2010 | Jones et al. |
| 8,019,125 B2 | 9/2011 | Nadreau et al. |
| 8,397,670 B2 | 3/2013 | Van Den Berg |
| 9,741,108 B2 | 8/2017 | Ikeda et al. |
| 10,442,633 B2 * | 10/2019 | Ooba ..................... B25J 9/1697 |
| 2001/0035370 A1 | 11/2001 | Yavnai et al. |
| 2005/0154490 A1 * | 7/2005 | Blaine ..................... B26D 5/32 700/186 |
| 2008/0195064 A1 | 8/2008 | Correa et al. |
| 2009/0000915 A1 | 1/2009 | Nadreau et al. |
| 2010/0059608 A1 | 3/2010 | Obata et al. |
| 2010/0310589 A1 | 12/2010 | Kumar |
| 2011/0106025 A1 | 5/2011 | Hall et al. |
| 2011/0217322 A1 * | 9/2011 | Purswell ................ A61D 1/025 424/184.1 |
| 2014/0336618 A1 | 11/2014 | Wilkerson et al. |
| 2015/0144071 A1 | 5/2015 | Samson et al. |
| 2015/0148771 A1 | 5/2015 | Samson et al. |
| 2015/0320010 A1 | 11/2015 | Schippers |
| 2017/0360540 A1 | 12/2017 | Jackwood et al. |

FOREIGN PATENT DOCUMENTS

| | | |
|---|---|---|
| JP | H05-253257 A | 10/1993 |
| JP | 10192310 A * | 7/1998 |
| JP | 1998192310 | 7/1998 |
| JP | 2007-044529 | 2/2007 |
| KR | 101278630 B1 | 6/2013 |
| WO | 2012008843 A1 | 1/2012 |
| WO | 2015112786 A1 | 7/2015 |
| WO | WO2018037417 A1 | 3/2018 |

OTHER PUBLICATIONS

English translation of Office Action issued by Federal Service for Intellectual Property (Russia) against Application No. 2018117356/10(027024) dated Mar. 4, 2020.
Substantive Examination Report issued by Directorate General of Intellectual Property (Indonesia) against Application No. PID201804018 dated May 27, 2020.
English summary, dated Jun. 3, 2020, of Substantive Examination Report issued by Directorate General of Intellectual Property (Indonesia) against Application No. PID201804018 dated May 27, 2020.
Communication pursuant to Article 94(3) EPC from the European Patent Office against Application No. 16865084.4-1011 dated Mar. 12, 2020.
Office Action issued by National Institute of Industrial Property (Brazil) against Application No. BR112018009633-4 dated Jun. 9, 2020 (5 pages).
English translation of Office Action issued by Federal Service for Intellectual Property Brazil) against Application No. BR112018009633-4 dated Jun. 9, 2020 (2 pages).
Second Office Action issued by National Intellectual Property Administration (China) against Application No. 201680065820.6 dated Jul. 21, 2020 (10 pages).
English translation of Second Office Action issued by National Intellectual Property Administration (China) against Application No. 201680065820.6 dated Jul. 21, 2020 (11 pages).
Office Action issued by United States Patent and Trademark Office against U.S. Appl. No. 15/775,608 dated Jul. 17, (10 pages).
Second Office Action issued by National Intellectual Property Administration (China) against Application No. 201680065988.7 dated Jul. 31, 2020 (8 pages).
First Office ActionEnglish translation of Second Office Action issued by National Intellectual Property Administration (China) against 201680065988.7 dated Jul. 31, 2020 (3 pages).
First Office Action issued by National Intellectual Property Administration (China) against Application No. 201680065986.8 dated Jul. 22, 2020 (9 pages).
English translation of First Office Action issued by National Intellectual Property Administration (China) against Application No. 201680065986.8 dated Jul. 22, 2020 (13 pages).

* cited by examiner

AUTOMATIC SYSTEM AND METHOD FOR DELIVERING A SUBSTANCE TO AN ANIMAL

PRIORITY

This application claims priority from U.S. provisional patent application Ser. No. 62/254,737, filed Nov. 13, 2015, and U.S. provisional patent application Ser. No. 62/349,981 filed Jun. 14, 2016. The contents of each are incorporated herein in their entirety.

BACKGROUND

Bacterial, viral and fungal infections and other diseases are often prevented or treated through vaccination, or delivery of a drug to a subject. In all animals, and in particular, vertebrates or fish, and invertebrates, such as crustaceans, the delivery of vaccines, biologics and other medicine is often delivered to prevent disease, death or to maintain overall good health. In many livestock and fish operations, it is a challenge to ensure that all animals have been effectively treated. The number and variation in the size of the subject makes vaccination and delivery of other medicine to each subject a challenge.

Turning now to the poultry industry in particular, there are several current methods in which fertilized eggs or chickens are treated with medicine. These include:
1) Automated Vaccination in the hatchery performed "in ovo" (within the egg) on day 18 or 19;
2) Automated Vaccination in the hatchery performed "post-hatch";
3) Manual Vaccination in the hatchery performed "post-hatch";
4) Vaccination/Medication added to the feed or water in the "Growth Farm"; and
5) Vaccination/Medication sprayed on the chicks either manually or by mass-sprayers.

While the poultry industry spends over $3 billion on vaccines and other pharmaceuticals on annual basis, the return on their investment is not guaranteed due to the challenges with the manner in which the vaccines or other substances are delivered. Each aforementioned method has shown noticeable and significant inadequacies. The automated vaccination in the hatchery performed in ovo on E18/19 is highly popular. However, there are drawbacks with this method. In particular, many vaccines of interest are either not available for in ovo application and may not become available by the nature of the disease and/or the conjugates necessary to carry the active molecules/particles to be applied in ovo. In addition, current practice of in ovo vaccination requires the punching/piercing of a whole in the egg on day 18 or 19. The delivery requires holding the egg in place by some mechanical means while extending a needle into the egg and administering the injection of the vaccine/drug. This practice may allow pathogens and bacteria to enter the egg and negatively impact the embryo. During the in ovo vaccination, undesirable eggs (rotten or eggs containing dead embryos) are also in contact with the mechanical means of holding eggs in a stationary position before getting punched/pierced and the needles. Thus there is a high probability of spreading undesirable contamination into other eggs and the vaccination system. Thus allowing transfer of contamination to subsequent live eggs during further processing.

To reduce the impact of this contamination transfer, the industry started to introduce and inject antibiotics into eggs as a part of in ovo vaccination. However, consumers are moving away from poultry treated with antibiotics. As such the industry is feeling the need to find alternative methods to treat the same diseases in a different manner that will maintain flock health while eliminating the use of antibiotics.

The "post-hatch" automated vaccination in the hatchery is performed after hatch but before chicks are counted and transported to a growth farm. The current post-hatch vaccination method utilizes a variety of mass sprayer systems which spray a large group of day old chicks with vaccines and other medication concurrently. These systems have proven to be inadequate in delivering of vaccines and medications to all chicks. The spray nozzles deliver an aspirated dosage to a group of chicks above their heads with the majority of droplets landing on the surface of the chick's heads and bodies resulting in chicks that do not receive the effective dosage. In addition, some chicks hide under the bodies of other chicks. As a result, they may not be exposed to the spray at all and thus not be effectively vaccinated. Chicks that are ineffectively vaccinated are a risk not only to themselves as they may catch a particular disease, but are also a risk to all of the other chicks around them. A single unvaccinated chick can spread disease to an entire farm and infect any other chick in the flock that was not vaccinated or not effectively vaccinated.

While "post-hatch" manual vaccination in the hatchery may be considered more reliable than other methods, studies have shown that this practice also is lacking in reliability and causes chick injuries and death. Hatcheries face challenges in finding reliable vaccinators and labor costs as increasing daily production rates. This heightens the challenge to ensure all chicks are effectively vaccinated which adds to the overall cost. In addition, because the chicks must be handled during vaccination, there is a risk of injury or death to the chick in the event the chick is harmed during handling. Moreover, because the workers must vaccinate multitudes of chicks, the workers are subject to repetitive stress injuries. This results in an economic and productivity loss to the poultry producers.

An alternative approach has been to add the vaccination/medication to the feed or water in the farm. This methodology has proven to be only partially effective, due to the fact that for the most part bacteria, pathogens and parasites in the chick's digestive system have become resistant to the drugs. Other factors that contribute to partial efficacy of this method include the lack of uniformity in the drinking lines, uneven doses delivered as a result of uneven amounts eaten or drunk, and that some vaccines have a very short half-life in water or feed.

The inadequacies of present vaccination methodologies combined with new market trends to eliminate the application of antibiotics in the poultry production, including the medicated feed additives ("MFAs"), are the main drivers for the embodiments described herein. Substance delivery via the mucosa, or mucous membrane, is effective and efficient when delivered properly. The challenge in mass delivery is ensuring that each animal has received the effective dose.

SUMMARY

The embodiments described herein are directed to a system and method for automatically delivering a substance to a predetermined area of an animal. The system includes a positioning device that positions an animal singularly and an image capture device that captures at least one image of the animal. The system further includes a computer processor that receives and transmits data and a delivery device for delivering a substance to the predetermined area. The image capture device shares the image with the computer processor which activates the delivery device to deliver the substance to the targeted area.

DESCRIPTION OF THE DRAWINGS

Figure 1:
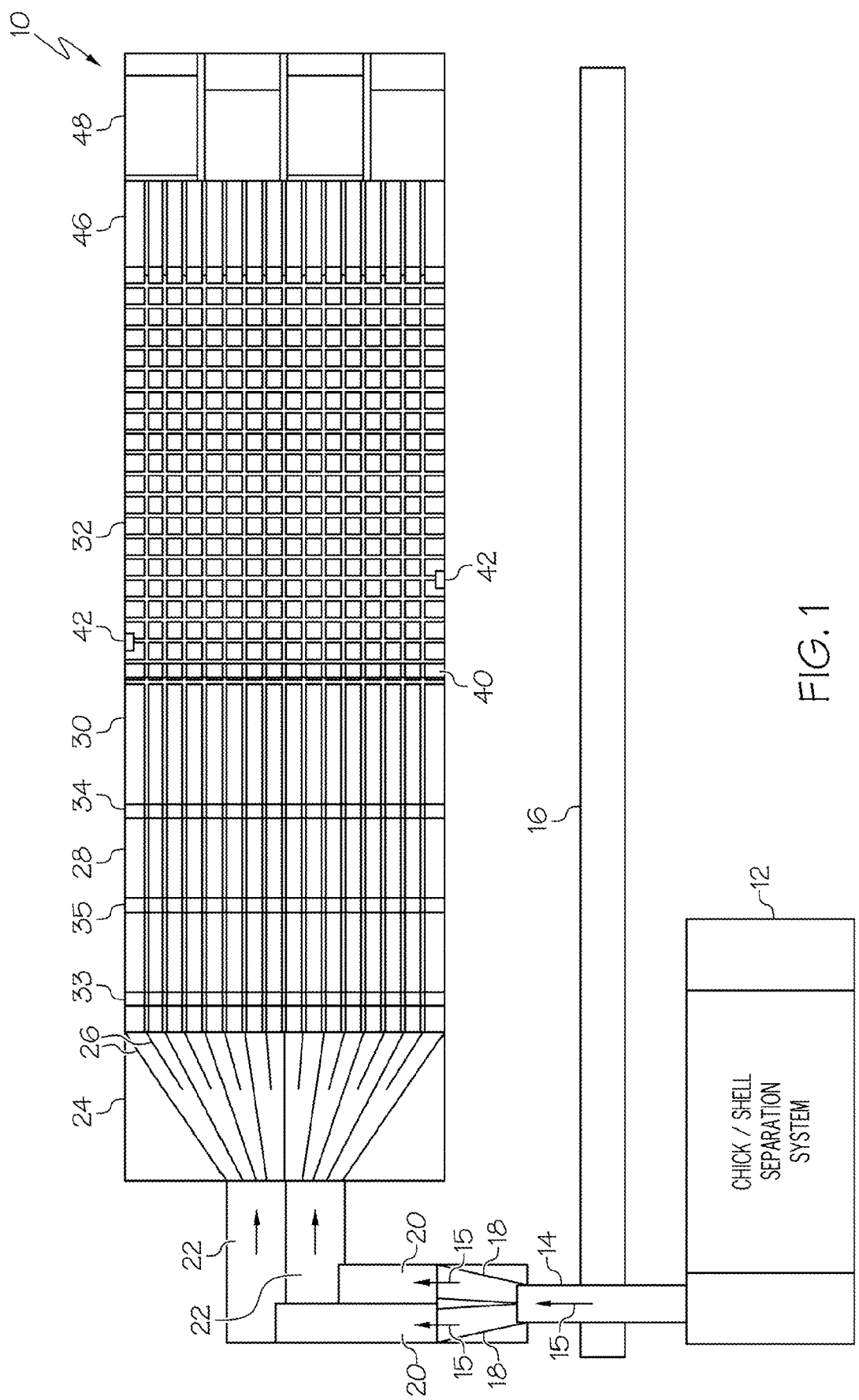
Figure 2:
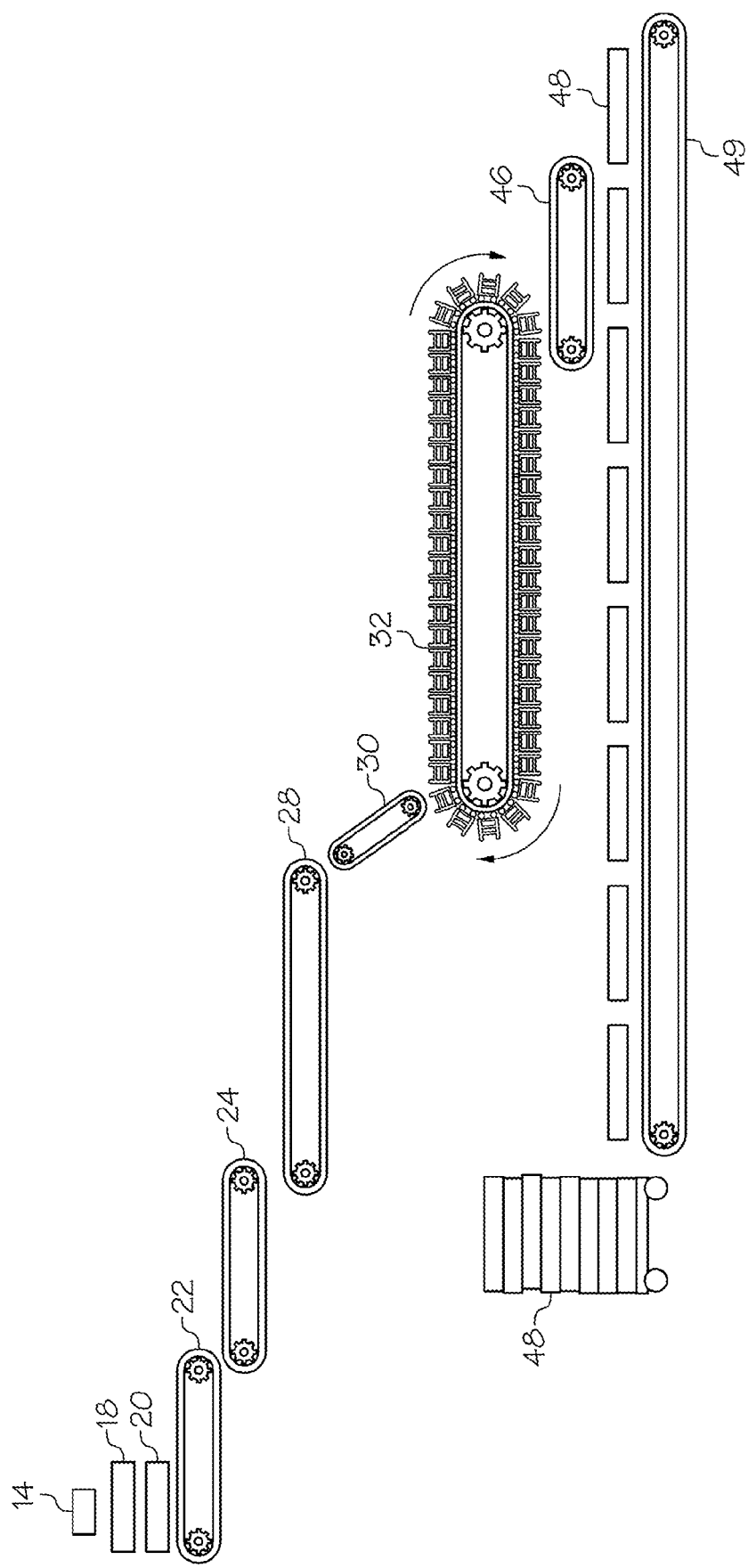
Figure 3:
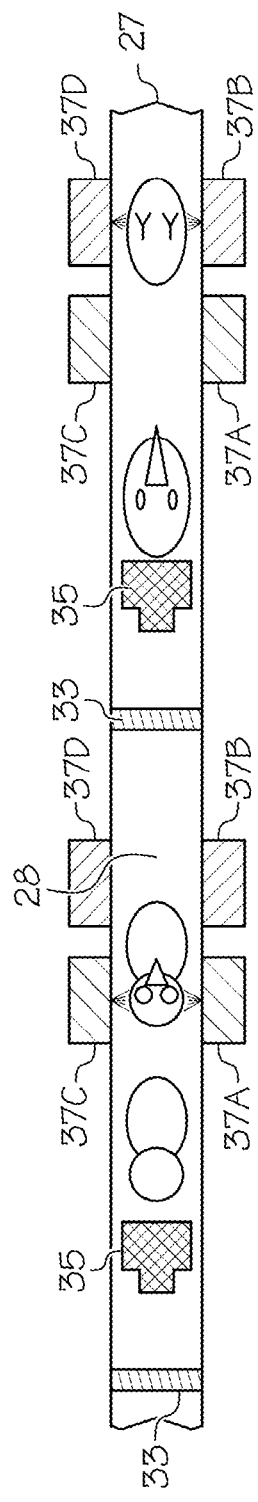
Figure 4:
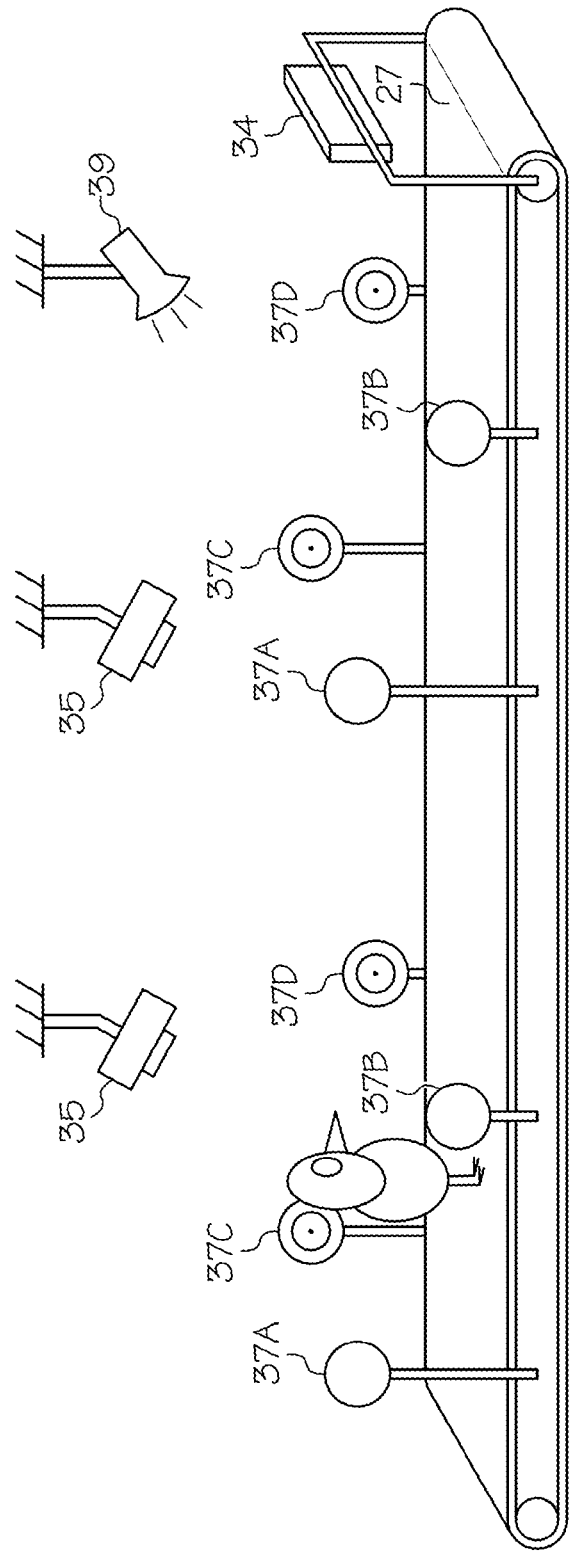
Figure 5:
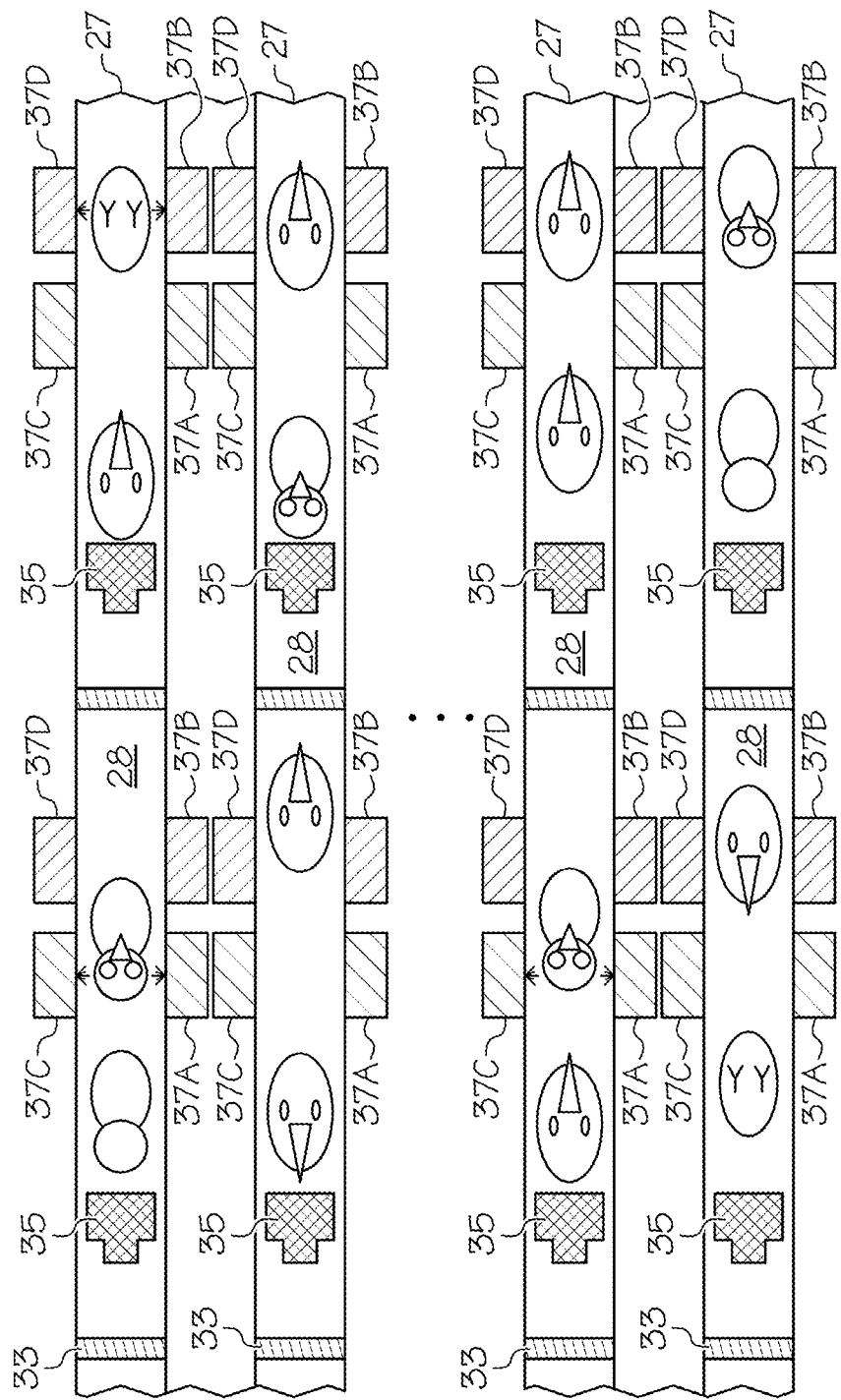
Figure 6:
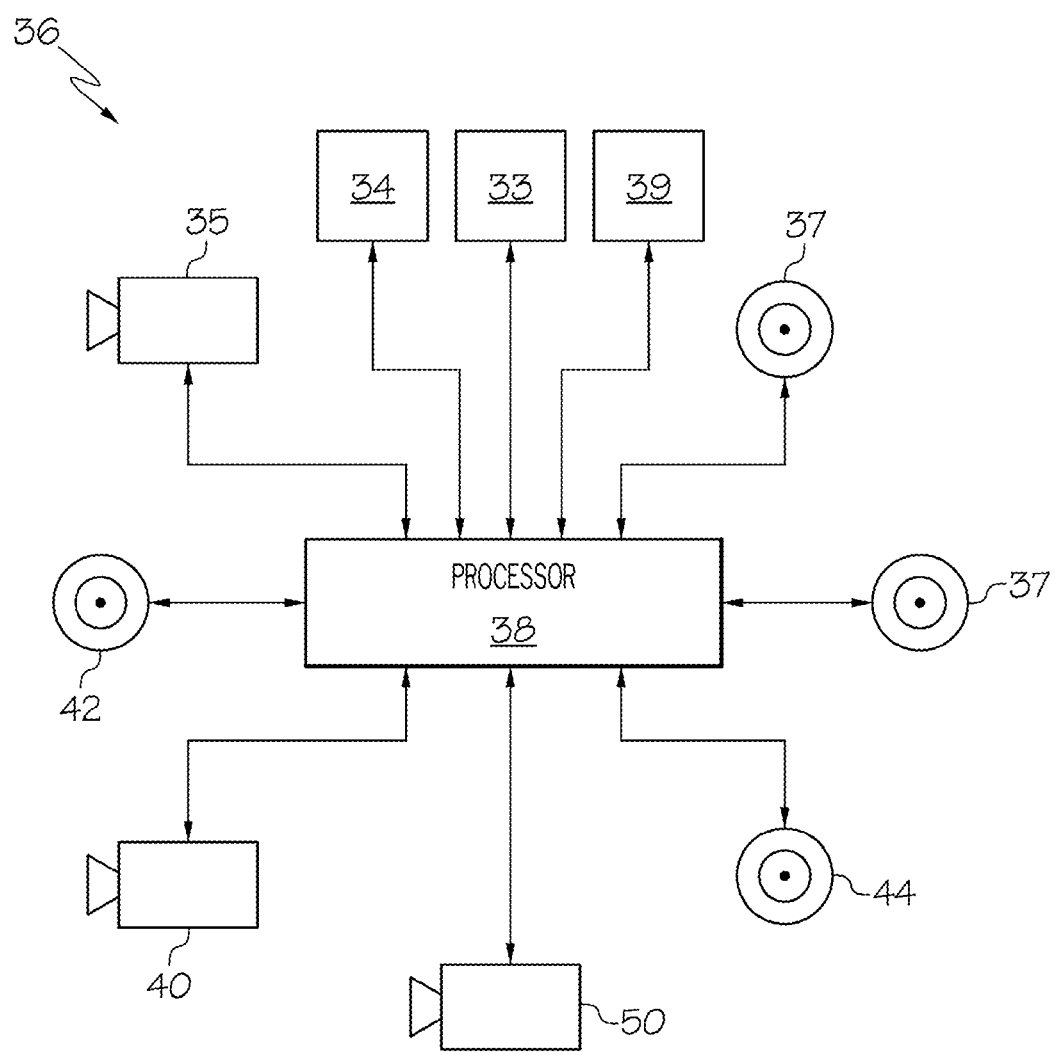
Figure 7:
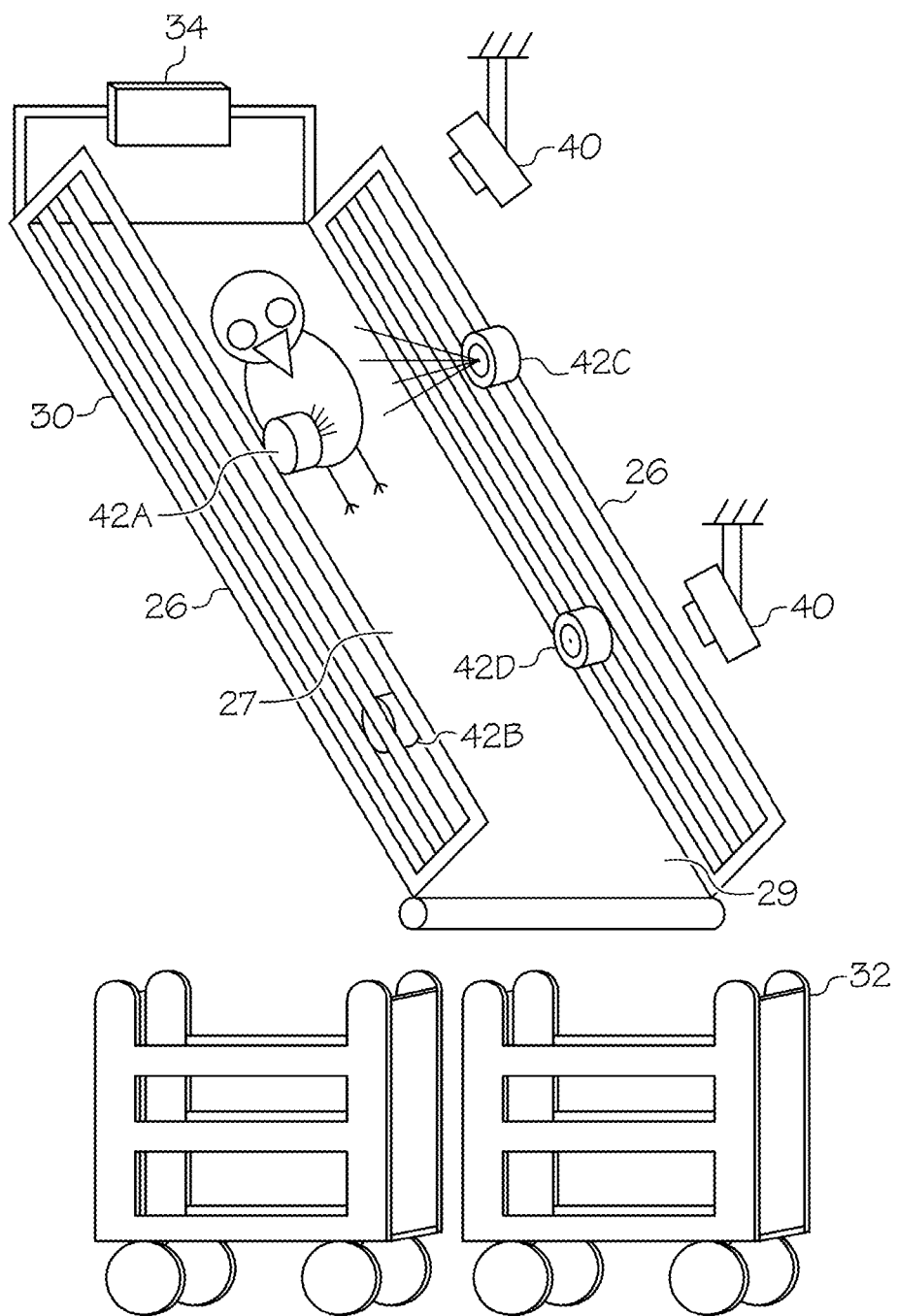
Figure 7A:
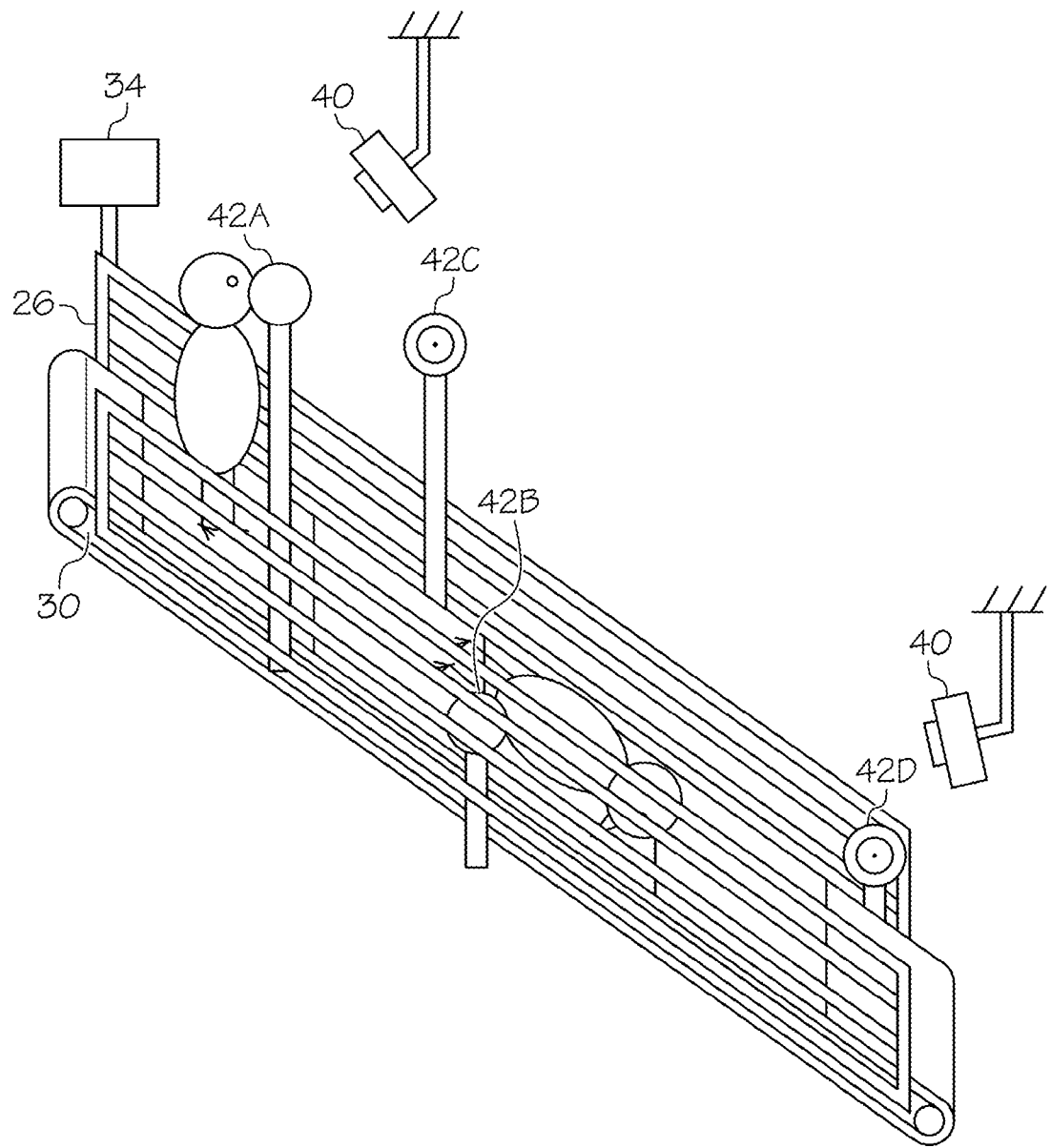
Figure 8:
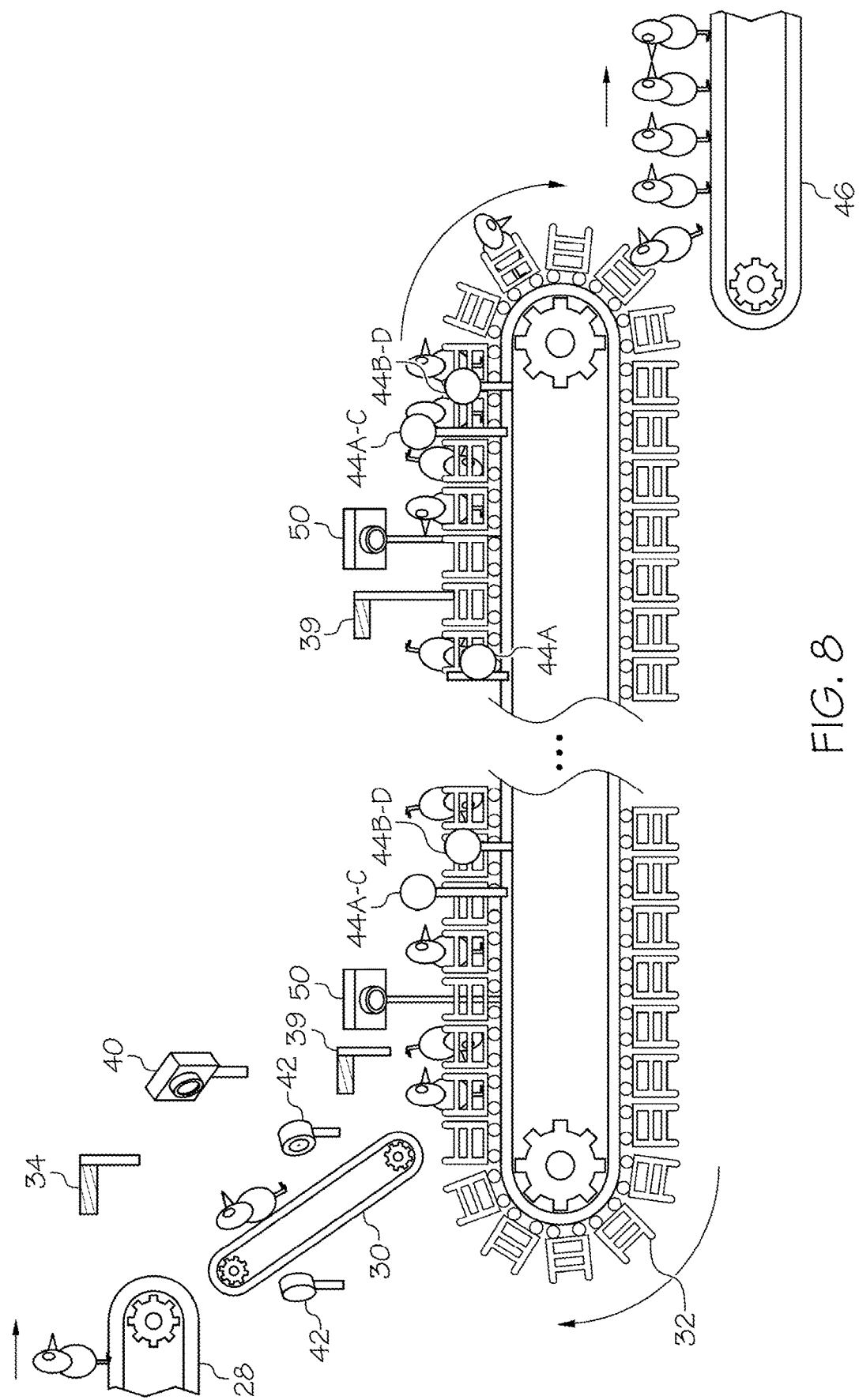
Figure 9:
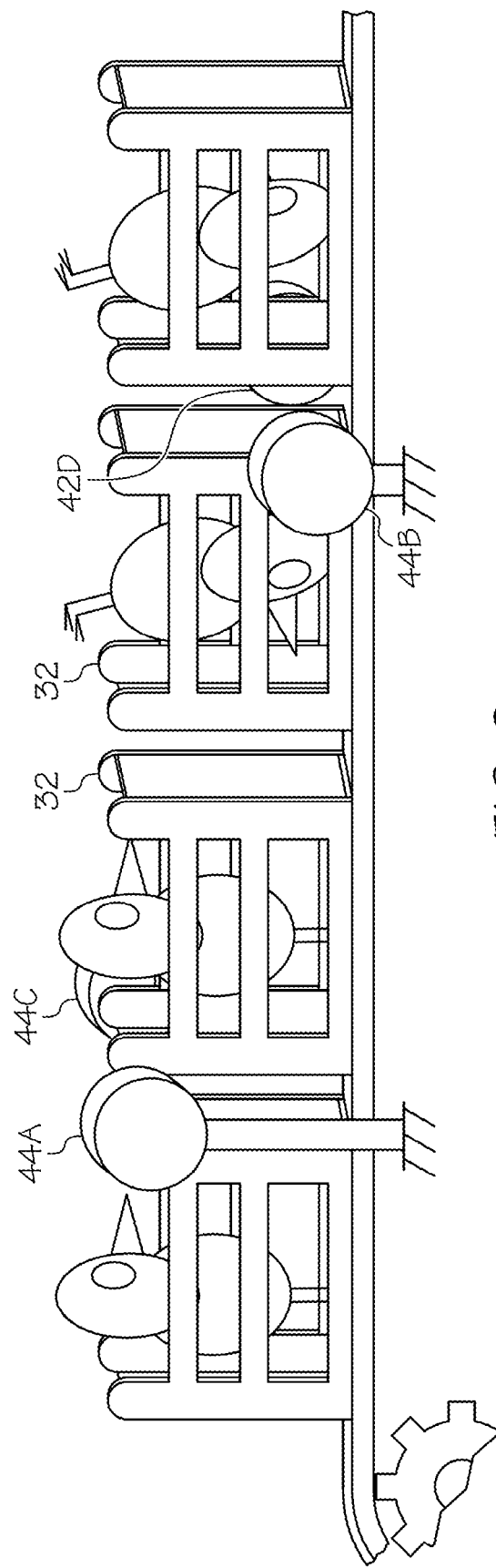
Figure 10:
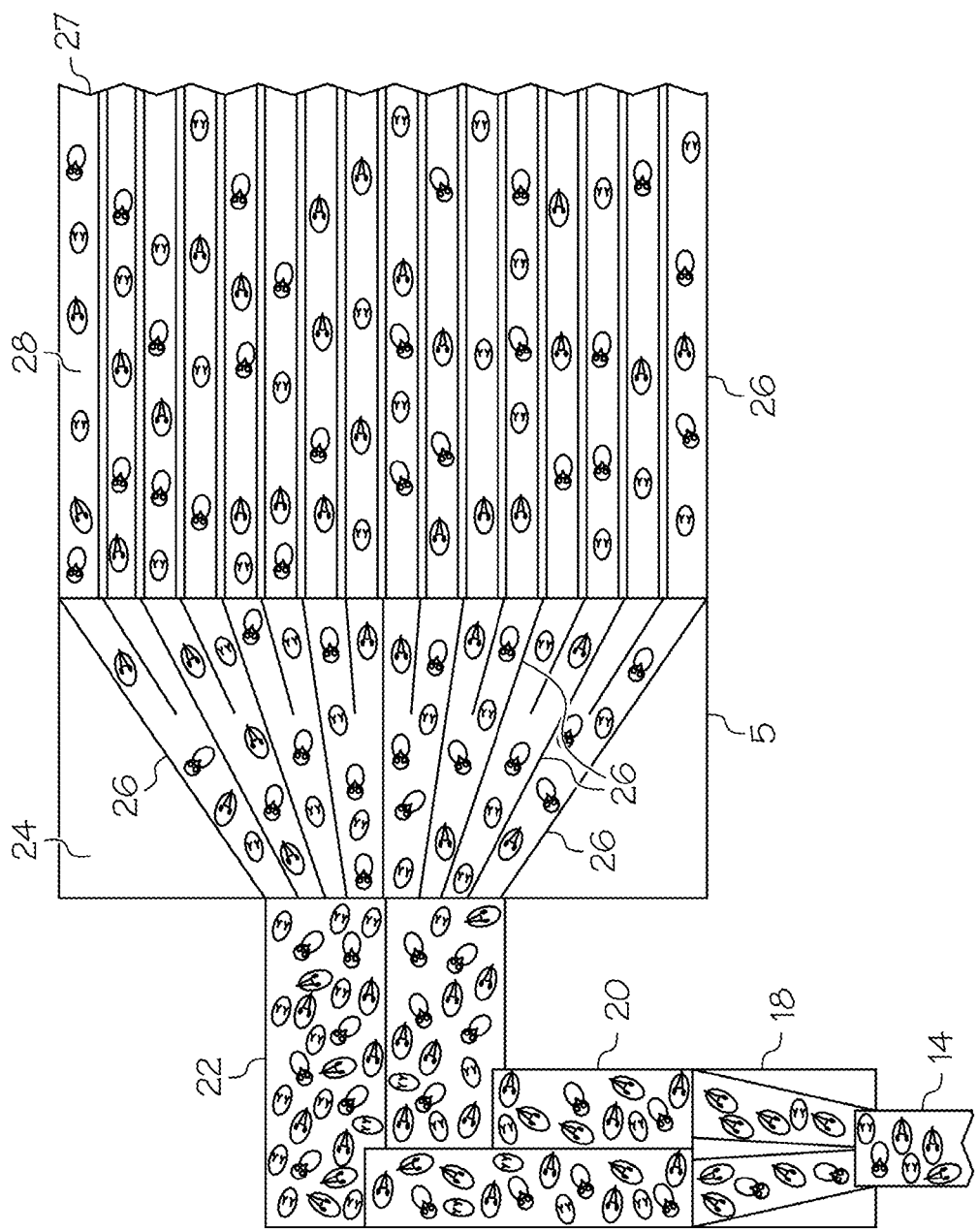

Having thus described various embodiments of the present disclosure in general terms, reference will now be made to the accompanying drawings, which are not drawn to scale and do not include all components of the system, and wherein:

FIG. 1 is a simplified schematic top view of a first embodiment;

FIG. 2 is a simplified schematic side view of the embodiment of FIG. 1;

FIG. 3 is an enlarged top view of a portion of the embodiment of FIG. 1 in use;

FIG. 4 is a side perspective view of the embodiment of FIG. 3;

FIG. 5 is an enlarged top view of a portion of the embodiment of FIG. 1 in use;

FIG. 6 is a diagrammatic representation of the interface of some of the components of the first embodiment;

FIG. 7 is a partial enlarged perspective view taken of a portion of the embodiment of FIG. 1 in use;

FIG. 7A is a side view of the embodiment shown in FIG. 7;

FIG. 8 is an enlarged side view of a portion of the embodiment of FIG. 1 in use;

FIG. 9 is a partial enlarged perspective view of a portion of the embodiment shown in FIG. 8; and FIG. 10 is a partial enlarged top view of the embodiment of FIG. 1 in use.

DETAILED DESCRIPTION

The present disclosure is directed to automated systems and methods for effectively delivering a substance to an animal. Various aspects of the present disclosure will be described more fully hereinafter with reference to the accompanying drawings, in which some, but not all aspects of the disclosure are shown. Indeed, this disclosure may be embodied in many different forms and should not be construed as limited to the aspects set forth herein.

One embodiment is directed to the delivery of a substance to chicken hatchlings after they have been separated from their shells and prior to departure from the hatchery. In addition, methods and systems according to aspects of the present disclosure relating to chicks may be used with any type of poultry including, but not limited to, chicken, turkey, duck, geese, quail, pheasant, ostrich, exotic birds, and the like.

FIG. 1 illustrates a simplified schematic top view of the overall system of the first embodiment 10. The simplified view does not include some of the equipment provided in various areas of the first embodiment 10 which will be explained in detail below and shown in other more detailed views. Similarly, FIG. 2 illustrates a simplified schematic side view of the overall system of the first embodiment 10.

The first embodiment 10 would likely be located in the day-of-hatch room in a chicken hatchery. The first embodiment 10 includes a chick/shell separator 12. The chick/shell separator 12 provides a means for separating the hatchling from its shell. A first conveyor 14 moves the chick from the chick/shell separator 12 through an opening in the separating wall 16 to a second, wider conveyor 18 in the direction of arrow 15. The separating wall 16 separates the shell separating process from the substance delivery process.

The second, wider conveyor 18 begins the spread the chicks out which makes processing each individual chick easier. From the second conveyor 18, the chicks are transported in the direction of arrows 15 onto third, and forth conveyors 20, 22 respectively, which are both wider than the conveyor 18. A fifth conveyor 24 has dividers 26 which may be suspended from the top of the conveyance assembly. The dividers 26 create lanes 27 (shown in FIGS. 3, 4 and 5) which help to move the chicks into narrow rows which eventually become single file rows (FIG. 1).

A plurality of first presence sensors 33 are located along each lane 27 on the sixth conveyor belt 28 as shown in FIG. 3. First cameras 35 are also located along each lane 27 on the sixth conveyor belt 28 and are located downstream from the direction of travel from the first presence sensors 33 and first cameras 35. In addition, first spray heads 37 A-D are located in each lane 27 on the pathway of the sixth conveyor belt 28. The first spray heads 37 A-D vary in height and location. In particular, as shown in detail in FIG. 4, 37A is mounted in a taller position on the right hand side of the lane 27. Spray head 37B is mounted in a lower position on the right hand side of the lane 27. Conversely spray head 37C is mounted in a higher position on the left hand side of lane 27 and spray head 37D is mounted in a lower position on the left hand side. This is done so that the first spray heads 37 A-D will hit a predetermined target on the chick regardless of the chick's position in the lane 27.

It should be noted that spray heads 37 A-D in FIG. 4 are designed to emit a cone shaped plume of spray. Thus when a chick passes the spray heads 37 A-D either the higher 37 A and C, or lower 37 B and D mounted heads will provide between them an area of spray that will ensure effective delivery of the substance. FIGS. 3 and 5 show the expanse of the plume of spray.

A first strobe light 39 is also located proximate to the sixth conveyor belt 28. The first strobe light 39 causes the chick to chirp and thus open its mouth. In the event the vaccination or other medicament is being delivered mucosally, the first strobe light 39 may be activated to aid in oral delivery.

The first presence sensors 33, first cameras 35, first spray heads 37 A-D and first strobe light 39 are all in communication with an automated substance delivery network 36, shown schematically in FIG. 6. The network 36 includes a computer processor 38 that enables network components such as the first presence sensor 33, first camera 35 and first spray heads 37 A-C to communicate with each other. The function of the network 36 will be explained in more detail below.

A plurality of second presence sensors 34 are located at the end of the sixth conveyor belt 28 and along the angled conveyor belt 30 Each second presence sensor 34 is positioned to sense the presence of a chick moving along the lane 27 created by dividers 26 on either side of the angled conveyor belt 30. Second cameras 40 and a second spray heads 42 A-D are also located along the pathway 29 of the angled conveyor belt 30. Second presence sensors 34, second cameras 40 and second spray heads 42 A-D are all in communication with the automated substance delivery network 36.

As discussed above with respect to the first spray heads 37 (FIG. 5), each second spray head 42 (FIG. 7) has a spray range within which a plume of spray is delivered. When the chick encounters the plume of spray as it travels along the angled conveyor belt, an effective dosage of the sprayed solution is delivered. Each second spray head 42 is positioned to focus the plume of spray on a chick travelling along the pathway of the angled conveyor belt 30. Multiple second spray heads 42 A-D may be positioned along the pathway of the angled conveyor belt 30 to ensure that at least one second spray head 42 will be able to deliver a plume of spray to each chick regardless of the chick's position. For example, there are four second spray heads 42 mounted along the pathway of the angled conveyor belt 30: 42A, 42B, 42C and 42D as shown in FIG. 7. Two second spray heads 42A, 42B are mounted on the right side of the pathway and the remaining two 42C, 42D on the left. One second spray head 42A on the right side is directed to the right upper half of a chick's body if the chick were travelling along the pathway in an upright position. The other second spray head on the right side 42B is directed to the right lower half of a chick's body if the chick were travelling along the pathway in an upright position. Similarly, the second spray head mounted on the left side 42C is directed to the left upper half of a chick's body if the chick were travelling along the pathway in an upright position and the other left mounted spray head 42D is directed to the left lower half of a chick's body if the chick were travelling along the pathway in an upright position. This mounting design allows for the delivery of sprayed solution into at least one eye, the nasal cavity and/or the mouth of a chick traveling along the angled conveyor belt regardless of its position.

Individual carrier devices 32 are located below the angled conveyor belt 30. Each individual carrier device 32 is similar to a cup, cage or basket and sized to receive a single chick as shown in FIGS. 7 and 8. The individual carrier devices 32 are interlinked and travel along an individual carrier pathway advanced by a conveyor system. Each carrier device 32 is hingedly mounted relative to the conveyor system so that each device can rotate or pivot about its hinged connection as shown in FIG. 8.

The third set of cameras 50 are located along the pathway of the individual carrier devices 32 in FIG. 8. The third set of spray heads 44 are also mounted along the individual carrier device 32 pathway. Similarly to the first spray heads 37 and second spray heads 42 discussed above, each third spray head 44 has a spray range within which a plume of spray is delivered. Each third spray head 44 is positioned facing towards the individual carrier pathway and carrier device 32 so that when operated, the plume of spray would contact the chick in a predetermined area.

It is appreciated that the chicks may assume a variety of positions as each enters the individual carrier device 32 and moves along the individual carrier device pathway FIGS. 8 & 9. As a result, the third spray heads 44 must be arranged in such a manner as to ensure that the collective range of delivery of the spray heads 44 will reach the predetermined target area on each chick regardless of its position within the individual carrier device 32.

To ensure that all chicks receive an effective dosage from the third spray heads 44 A-D, the third set of spray heads are fixedly mounted at varying heights and/or angles along the individual carrier pathway. In the first embodiment 10, third spray heads 44 are fixedly mounted at higher 44A, 44C and lower 44B, 44D positions relative to the individual carrier devices 32, as shown in detail in FIG. 9. The purpose of this arrangement will become more apparent when the operation of the system is discussed in detail below.

Below the individual carrier devices 32 is a seventh conveyor belt 46 as shown in FIGS. 1, 2 and 8. The seventh conveyor belt 46 moves the chicks as they are emptied out of the individual carrier devices 32 and into containers 48 (FIG. 2) for transfer to a grow out farm where they will be grown for consumption.

Turning now to the operation of the first embodiment 10 described above, the chicks are moved from the chick/shell separator 12 onto the first conveyor 14 (FIG. 1). As they move along the first conveyor 14, the chicks pass through the separating wall 16 which separates the hatching process from the substance delivery process.

From the first conveyor 14, the chicks are moved onto the second, third, and fourth conveyors 18, 20, 22 respectively in the direction of arrows 15. These conveyors 18, 20, 22 are designed to move the chicks along the processing pathway and spread them out so that they are ready to form single rows with guidance as will be explained below. The chicks move from the fourth conveyor 22 to the fifth conveyor 24 which gradually widens and includes dividers 26. The graduated width and dividers 26 aid in moving the chicks further apart and help form single rows. The chicks move in single rows from the fifth conveyor 24 onto the sixth conveyor 28. The dividers 26 on the sixth conveyor 28 create single rows in which only a single chick can pass at any given point. This is shown in FIG. 10.

Once the chick is on the sixth conveyor 28, as shown in FIGS. 3, 4 and 5, a first presence sensor 33 senses the presence of a chick within a given lane 27. The first presence sensor 33 signals the automatic substance delivery system 36 which signals the first camera 35 (FIG. 4). The first camera 35 creates at least one image of the chick as it advances along the lane 27 on the sixth conveyor 28. The image is relayed back to the computer processor 38 within the automatic substance delivery system 36 which processes the image to determine the relative position of the targeted area on the chick. Based on the processor's determination of the position of the targeted area, the delivery system 36 signals one of the first spray heads 37 to activate. For example, if the image sent from the first camera 35 to the computer processor 38 indicates that the chick is lying on its back and the targeted area is predetermined to be the facial mucosa, then the computer processor would signal the shortest first spray head 37C to activate. The shortest first spray head 37C would deliver a plume of spray to the chick's facial region so that an effective dosage of substance would be delivered to the chick's eye, mouth and or nasal cavity.

In addition, the first strobe light 39 may (FIG. 4) be activated by the computer processor 38. This would result in the chick chirping upon seeing the intense pulses of light. The chick's open mouth may receive a dosage of substance either directly or indirectly from one or more of the spray heads 37.

After the chick has traveled along the sixth conveyor belt 28, the chick drops onto the angled conveyor belt 30 shown in FIG. 7. The chick's presence on the single lane pathway of angled conveyor belt 30 created by the dividers 26 is signaled to the computer processor 38 by a second presence sensor 34. The signal from the second presence sensor 34 activates the second camera 40. Camera 40 captures at least one image of the chick as it passes along the pathway of the angled conveyor belt 30. The image is transmitted to the computer processor 38 and processed to determine the position of the chick.

Once the position of the chick is determined by the computer processor 38, a signal is sent to one of the second spray heads 42 at a particular location to activate at a particular time. The activation is timed so that the second spray head 42 delivers a plume of substance, such as a vaccine or other medicament, into the facial mucosa of the chick as it is passing along the angled conveyor pathway, as shown in FIG. 7A. For example, if the chick is traveling upright on its back along the angled conveyor belt 30, the computer processor 38, having determined the position of the chick and rate of travel, may activate the right upper second spray head 42A at a specific time. This will deliver a plume of spray into the right eye of the chick as it passes.

The timely activation of the second spray head 42 in FIG. 7A enables the substance to be distributed to all facial mucosa including the eyes, nasal cavity and mouth, without significant waste and at the effective dosage. In addition, the timely activation of the second spray head 42 ensures that each chick passing through the angled conveyor belt 30 will receive an effective dosage of the substance.

It is envisioned that additional second spray heads 42 may be provided to deliver more than one substance to the chicks traveling along the angled conveyor belt 30 as needed. For example, if spray heads 42A, 42B, 42C and 42D as described above, were delivering a first vaccine to a chick. Additional spray heads 42E, 42F, 42G and 42H may be similarly positioned as described above to deliver a second vaccine or other medicament to the chick as it travels along the angled conveyor belt 30 pathway as shown in FIG. 6.

Once the chick has passed through the angled conveyor belt 30, the chick lands within one of the individual carrier devices 32, as shown in FIG. 8. A third camera 50 is mounted proximate to the location where the chick enters the carrier device 32. The image is taken by the camera 50 of the chick in the individual carrier device 32. The image is communicated to the computer processor 38 and processed to determine the relative position of the chick. Once the computer processor determines the relative position of the chick's facial mucosa while positioned within the individual carrier, then the computer processor 38 activates the third spray head 44 best positioned to achieve effective delivery. For example, if the chick is positioned upside down in the individual carrier device 32, the computer processor may activate second spray head 44A at a specific time. In this manner, the chick will obtain a plume of spray in one of its eyes as its carrier device 32 passes spray head 44A (FIG. 8).

As with the previous delivery, the third spray head 44 is able to deliver an effective dosage to the facial mucosa of each chick processed through the system. In this manner, each chick will receive the appropriate dosage and the flock as a whole will be healthier and more robust. Similarly as described above, it is envisioned that additional third spray heads may be employed to deliver additional substances to the chicks while they are positioned within the carrier devices 32. For example, a medicament may be delivered to chicks by means of third spray heads 44A, and 44B, and a vaccine or other substance may be delivered to chicks by means of additional third spray heads 44C and 44D of low and high heights relative to the carrier device 32 respectively.

It should be appreciated that while the first embodiment 10 provides for delivery of a substance along the sixth conveyor belt 28, the angled conveyor belt 30 and in the individual carrier device 32, all are not necessary. For example, it may be appropriate in one situation to deliver substance to the chicks along the angled conveyor belt 30 while in another situation, it may be more appropriate to deliver substance to the chicks while they are in the carrier device 32. Conversely, it may be appropriate to delivery different substances at varying stages of processing. For example, it may be desired to deliver a first substance or vaccine to the chicks as they travel along the sixth conveyor belt 28, a second substance or vaccine as they travel along the angled conveyor belt 30, and a third substance or vaccine as they travel in the individual carrier devices 32.

At the end of travel of the carrier device 32, the device pivots about its hinged connection and the chick is emptied out and placed on a seventh conveyor belt 46. This seventh conveyor belt 46 drops the chicks into containers 48. The containers 48 may travel along an eighth conveyor belt 49 before they are collected for moving to a different location for further processing.

It should also be noted that the first embodiment described above is directed to the automated delivery of a substance to the mucosa of a bird. The embodiments described herein would also apply to the automated delivery of a substance to the mucosa of any other animal, such as a human, and other livestock. It is envisioned that certain medicaments for cattle, or sheep may be delivered in an automated manner to either the facial mucosa or vaginally or anally as required in a particular application.

It is anticipated that the types of vaccines or other substances given to chicks by spray application to the mucosa may include, but not be limited to the following: vaccinations against Newcastle disease, infectious bronchitis virus, *E coli, salmonella*, coccidia, and camplyobactor.

It is also anticipated that the embodiments herein may apply to the automated delivery of substance to the mucosa of other animals and mammals, including humans. In particular, there may be certain applications that may be appropriate for automated delivery of a substance to the facial mucosa of an infant or child, or disabled person. In addition, the automated delivery system described herein may have applicability to other animals, such as livestock, rodents and other animals raised commercially.

It is expected that many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not intended to be limited to the specific aspects disclosed and that modifications and other aspects are intended to be included within the scope of the appended claims. Although specific terms are employed herein, they are used in a generic and descriptive sense only and not for purposes of limitation.

The invention claimed is:

1. A system for automatically delivering a substance to an eye of an animal comprising:
    a positioning device that positions an animal along a moving platform;
    an image capture device to capture at least one image of the relative position of the eye of an animal as the animal is being conveyed on the moving platform;
    a substance spray delivery system having at least one delivery spray nozzle, the nozzle capable of delivering a plume of spray at least as wide as the width of the animal's eye, the nozzle being located along the pathway of the moving platform; and
    a computer processor in communication with the image capture device, and the spray system, whereby the image capture device captures at least one image of the relative position of the eye of the animal and shares the image with the computer processor, the computer processor processes the image, determines the relative position of the eye of the animal and activates the spray nozzle to deliver the plume of spray of the substance to the animal.

2. The system of claim 1 wherein the spray nozzle delivers a conical shaped plume of spray.

3. The system of claim 1 wherein the positioning system comprises a container for containing a singular animal.

4. The system of claim 1 wherein the animal is a bird.

5. The system of claim 4 wherein the animal is a chicken.

6. The system of claim 1 wherein the substance is a vaccine, medicament or biologic.

7. The system of claim 1 wherein the substance is intended to treat one or more of the following: Newcastle disease, infectious bronchitis, coccidiosis, *E coli, salmonella*, or camplyobactor.

8. An automated system for delivering a substance to the eye of an animal comprising:
- a positioning device for positioning an animal individually;
- an image capture device for capturing at least one image of an eye on the animal for delivery of a substance;
- a spray system comprising a reservoir of substance, a pressurized gas supply, at least one delivery spray head, the spray head capable of delivering a plume of spray at about as wide as the animal's eye; and
- a computer processor, the computer processor in communication with the image capture device and spray system, whereby when an animal is positioned individually, the image capture device captures at least one image of the animal's eye and communicates the image to the computer processor, the computer processor processes the image and activates at least one delivery spray head to spray a plume of substance into at least one eye on the animal.

9. The system of claim 8 wherein the plume of spray is conical.

10. The system of claim 8 wherein the substance is a vaccine, medicament or biologic.

11. The system of claim 8 wherein the substance is intended to treat one or more of the following: Newcastle disease, infectious bronchitis, coccidiosis, *E coli, salmonella*, or camplyobactor.

12. The system of claim 8 wherein the positioning device includes at least one conveyor belt.

13. The system of claim 8 wherein the image capture device comprises at least one camera.

\* \* \* \* \*